(12) United States Patent
Kulkarni et al.

(10) Patent No.: US 8,611,066 B2
(45) Date of Patent: Dec. 17, 2013

(54) NON-RADIOACTIVE BIPOLAR CHARGER FOR AEROSOL PARTICLES

(75) Inventors: Pramod Kulkarni, Mason, OH (US); Chaolong Qi, Cincinnati, OH (US)

(73) Assignee: Centers for Disease Control and Prevention, Atlanta, GA (US)

( * ) Notice: Subject to any disclaimer, the term of this patent is extended or adjusted under 35 U.S.C. 154(b) by 186 days.

(21) Appl. No.: 13/315,344

(22) Filed: Dec. 9, 2011

(65) Prior Publication Data

US 2013/0148252 A1 Jun. 13, 2013

(51) Int. Cl.
*H01H 47/00* (2006.01)
(52) U.S. Cl.
USPC .......................................... 361/231; 361/220
(58) Field of Classification Search
USPC ........................................ 361/212, 220, 231
See application file for complete search history.

(56) References Cited

U.S. PATENT DOCUMENTS

| 6,145,391 | A | 11/2000 | Pui et al. |
| 7,031,133 | B2 | 4/2006 | Riebel et al. |
| 7,855,868 | B2 | 12/2010 | Taishi et al. |
| 2009/0304945 | A1 * | 12/2009 | Brown et al. ................. 427/462 |

OTHER PUBLICATIONS

Motoaki Adachi, David Y.H. Pui & Benjamin Y.H. Liu, "Aerosol Charge Neutralization by a Corona Ionizer," *Aerosol Science and Technology*, 18:1, 48-58 (1993).

* cited by examiner

*Primary Examiner* — Danny Nguyen
(74) *Attorney, Agent, or Firm* — Gifford, Krass, Sprinkle, Anderson & Citkowski, P.C.; Douglas L. Wathen (57) ABSTRACT

A bipolar charger includes a housing with a main chamber and positive and negative electrode chambers facing each other. The electrode chambers each have a ground electrode and a high voltage electrode that cooperate to create a cloud of ions. An aerosol flowing from an inlet passage through the main chamber and out an outlet passage mixes with the clouds of ions, thereby providing an aerosol with a steady-state electric charge distribution.

19 Claims, 8 Drawing Sheets

NON-RADIOACTIVE BIPOLAR CHARGER FOR AEROSOL PARTICLES

GOVERNMENT INTEREST

The invention described herein may be manufactured, used, and licensed by or for the United States Government.

FIELD OF THE INVENTION

This invention relates generally to bipolar chargers for providing a steady-state electric charge distribution to an aerosol.

BACKGROUND OF THE INVENTION

Bipolar chargers are used to provide a steady-state electric charge distribution to an aerosol. This is useful for a variety of tasks, including collection, analysis, and measurement of particles in an aerosol.

Aerosols may include charged particles, but the distribution of charges on the particles varies depending on a number of factors. For many applications, particularly for measurement applications, it is desirable to treat, or charge-condition, an aerosol such that it acquires a steady-state electric charge distribution. A bipolar charger may be used to provide such a steady-state electric charge distribution. Certain bipolar chargers operate by providing a mixture of positive and negative ions. This mixture of positive and negative ions is mixed with the aerosol resulting in bipolar diffusion charging. If the ion populations are initially balanced, the charge state of their aerosol will eventually reach a quasi-steady state.

Most bipolar chargers use a radioactive source, which leads to regulatory and transportation issues. This is a major obstacle in conducting field measurements of aerosols using instruments that utilize such radioactive sources. As such, there is a need for a bipolar charger that does not include a radioactive source, is capable of being miniaturized, and is low in cost.

SUMMARY OF THE INVENTION

The present invention provides embodiments of a bipolar charger and methods for providing an aerosol with a steady-state electric charge distribution. According to one embodiment, a bipolar charger for charging particles of a flow of aerosol includes a housing with a main chamber, a positive electrode chamber, and a negative electrode chamber defined therein. The electrode chambers are each directly connected to the main chamber and each have an inner surface. An inlet passage allows a flow of aerosol into the main chamber and has an inner surface formed of an electrically conductive material. An outlet passage allows charged aerosol to flow from the main chamber and also has an inner surface formed of an electrically conductive material. A flow path for the aerosol is defined from the inlet passage, through the main chamber, and out of the outlet passage. A first ground electrode is disposed in the positive electrode chamber. A positive electrode is disposed in the positive electrode chamber and spaced from the first ground electrode. A second ground electrode is disposed in the negative electrode chamber. A negative electrode is disposed in the negative electrode chamber and spaced from the second ground electrode. A power supply is interconnected with the first and second ground electrodes and the positive and negative electrodes. A first corona current is maintained between the positive electrode and the first ground electrode such that the positive electrode is at a high positive potential with respect to the first ground electrode and the positive electrode and the first ground electrode cooperate to create a cloud of positive ions. A second corona current is maintained between the negative electrode and the second ground electrode such that the negative electrode is at a high negative potential with respect to the second ground electrode and the negative electrode and the second ground electrode cooperate to create a cloud of negative ions. The first and second ground electrodes and the inner surfaces of the inlet and outlet passages are grounded relative to the positive and negative electrodes. The positive electrode chamber and the negative electrode chamber each are in gaseous communication with the main chamber such that particles of an aerosol passing along the flow path through the main chamber interact with the ions, thereby creating a flow of aerosol with a steady-state electric charge distribution.

In some versions, the first ground electrode defines a portion of the inner surface of the positive electrode chamber and the second ground electrode defines a portion of the inner surface of the negative electrode chamber. The inner surfaces of the electrode chambers not defined by the ground electrodes may be formed of a dielectric material. The first ground electrode may take the form of a pair of electrode plates each defining portions of the inner surface of the positive electrode chamber, and each being spaced from the positive electrode. The second ground electrode may take the form of a pair of electrode plates each defining portions of the inner surface of the negative electrode chamber, and each being spaced from the negative electrode. The electrode plates in the positive electrode chamber may define opposed inner surfaces, with the surfaces being angled with respect to each other at an angle in the range of 0 to 70 degrees. The electrode plates in the negative electrode chamber may define opposed inner surfaces, with the surfaces being angled with respect to each other at an angle in the range of 0 to 70 degrees. The positive and negative electrodes may each have a longitudinal axis that is parallel to the planes containing the electrode plates. Each electrode chamber may be said to have a chamber axis defined midway between the ground plates. The chamber axis of the positive electrode chamber may be angled with respect to the chamber axis of the negative electrode chamber at an angle in the range of 0 to 70 degrees.

In some versions of the bipolar charger, the inlet passage has an inlet axis and the electrode chambers are symmetrical with respect to the inlet axis and configured such that the positive electrode is not directly exposed to the negative electrode.

In certain embodiments, the first ground electrode is a member dividing the positive chamber from the main chamber and the second ground electrode is a member dividing the negative electrode chamber from the main chamber. These members each have a plurality of openings defined therethrough such that the clouds of ions may pass through the openings from the electrode chambers to the main chamber. In some versions, the openings in the electrode members each have an opening size in the range of 20 micron to 1 millimeter and the electrode members have an open area in the range of 20 to 90 percent of their total area.

In some embodiments of the bipolar charger, the inlet passage and outlet passage comprise a tube with a mid portion defined between an inlet portion and an outlet portion. The inlet portion defines the inlet passage and the outlet portion defines the outlet passage. The mid portion forms part of the main chamber of the housing and has at least one opening defined therein such that the particles of the flow of aerosol along the flow path interact with ions in the main chamber. The tube may be a metal tube and in some versions has a pair of opposed openings in the mid portion, with each opening facing one of the electrode chambers.

In some embodiments of the bipolar charger, the positive and negative electrodes are each needle shaped with an exposed tip, the electrodes having a diameter in the range of 50 to 500 microns and a tip radius in the range of 5 to 100 microns.

In certain embodiments, the power supply comprises two power supplies, with each power supply providing the corona current to one of the positive or negative electrodes, and the corona currents being in the range of 1 to 10 microamperes. The power supplies may include Proportional, Integral, Derivative (PID) controls for controlling the corona current.

A further embodiment of a bipolar charger in accordance with the present invention includes a housing with a main chamber, a positive electrode chamber, and a negative electrode chamber defined therein. The electrode chambers each have an inner surface. A first ground electrode member is disposed in the housing so as to divide the positive electrode chamber from the main chamber. The first ground electrode member defines a portion of the inner surface of the positive electrode chamber. A second ground electrode member is disposed in the housing so as to divide the second electrode chamber from the main chamber. The second ground electrode member defines a portion of the inner surface of the negative electrode chamber. An inlet passage allows a flow of aerosol into the main chamber and has an inner surface formed of an electrically conductive material. An outlet passage allows charged aerosol to flow from the main chamber and has an inner surface formed of an electrically conductive material. A flow path for the aerosol is defined from the inlet passage, through the main chamber, and out of the outlet passage. A positive electrode is disposed in the positive electrode chamber and spaced from the first ground electrode member. A negative electrode is disposed in the negative electrode chamber and spaced from the second ground electrode member. A power supply is interconnected with the first and second ground electrodes and the first and second high voltage electrodes. A first corona current is maintained between the positive electrode and the first ground electrode such that the positive electrode is at a high positive potential with respect to the first ground electrode member and the positive electrode and the first ground electrode member cooperate to create a cloud of positive ions. A second corona current is maintained between the negative electrode and the second ground electrode member such that the negative electrode is at a high negative potential with respect to the second ground electrode member and the negative electrode and the second ground electrode member cooperate to create a cloud of negative ions. The ground electrode members each have a plurality of openings defined therethrough such that the clouds of ions may pass through the openings from the electrode chambers to the main chamber. The first and second ground electrode members and the inner surfaces of the inlet and outlet passages are grounded relative to the positive and negative electrodes. The positive electrode chamber and the negative electrode chamber are each in gaseous communication with the main chamber through the openings in the ground electrode members such that particles of an aerosol passing through the main chamber interact with the ions, thereby creating a flow of aerosol with a steady-state electric charge distribution.

In some versions of this embodiment of the bipolar charger, the inlet passage and outlet passage comprise a tube with a mid portion defined between an inlet portion and an outlet portion. The inlet portion defines the inlet passage and the outlet portion defines the outlet passage. The mid portion forms part of the main chamber of the housing. The mid portion has at least one opening defined therein such that the particles of the flow of aerosol along the flow path interact with ions in the main chamber. In some versions, the tube is generally parallel to the ground electrode members, with the ground electrodes being spaced from the outer surface of the tube by a distance in the range of 1 millimeter to 5 millimeter. As will be clear to those of skill in the art, these dimensions, and other dimensions provided herein, are for a particularly sized unit, and will change if the size of the whole unit is scaled up or scaled down.

In some versions of this embodiment of the bipolar charger, the electrode members comprise a mesh, a perforated plate, an orifice plate, or a screen. The openings in the electrode members each have a size in the range of 20 micron to 1 millimeter and the electrode members have an open area in the range of 20 to 90 percent of their total area.

The present invention also provides a method for providing a steady-state charge distribution to a flow of aerosol. The method comprises providing a bipolar charger for charging particles of a flow of aerosol. The bipolar charger includes a housing with a main chamber, a positive electrode chamber, and a negative electrode chamber defined therein. The positive electrode chamber and the negative electrode chamber each are directly connected to and in gaseous communication with the main chamber. The electrode chambers each have an inner surface. An inlet passage allows a flow of aerosol into the main chamber and has an inner surface formed of an electrically conductive material. An outlet passage allows charged aerosols to flow from the main chamber and has an inner surface formed of an electrically conductive material. A flow path for the aerosol is defined from the inlet passage, through the main chamber, and out of the outlet passage. A first ground electrode is disposed in the positive electrode chamber and a positive electrode is disposed in the positive electrode chamber and spaced from the ground electrode. A second ground electrode is disposed in the negative electrode chamber and a negative electrode is disposed in the negative electrode chamber and spaced from the second ground electrode. The method further comprises providing a flow of aerosol along the flow path. A first corona current is maintained between the positive electrode and the first ground electrode such that the positive electrode is at a high positive potential with respect to the first ground electrode and the positive electrode and the first ground electrode cooperate to create a cloud of positive ions. A second corona current is maintained between the negative electrode and the second ground electrode such that the negative electrode is at a high negative potential with respect to the second ground electrode and the negative electrode and the second ground electrode cooperate to create a cloud of negative ions. The first and second ground electrodes and the inner surfaces of the inlet and outlet passages are grounded relative to the positive and negative electrodes. This results in particles of the aerosol passing along the flow path and through the main chamber such that they interact with the ions from the electrode chambers, thereby creating a flow of aerosol with a steady-state electric charge distribution.

DETAILED DESCRIPTION OF THE PREFERRED EMBODIMENTS

The present invention provides several embodiments of a bipolar charger for charging particles of a flow of aerosol such that an aerosol flow is created with a steady-state electric charge distribution. Embodiments of the bipolar charger include a housing with a main chamber, a positive electrode chamber, and a negative electrode chamber defined therein. Each electrode chamber has a ground electrode, while one of the electrode chambers has a positive electrode and the other has a negative electrode. The positive electrode and the negative electrode may also be referred to as high voltage electrodes, since during operation they are maintained at a high voltage, either positive or negative, relative to the ground electrodes. Corona currents are maintained between the high voltage electrodes and their respective ground electrodes such that the high voltage electrodes and the ground electrodes cooperate to create a cloud of ions. These clouds of ions flow from the electrode chambers into the main chamber where they mix with an aerosol flowing through the main chamber. This results in the aerosol having a steady-state electric charge distribution.

Figure 1:
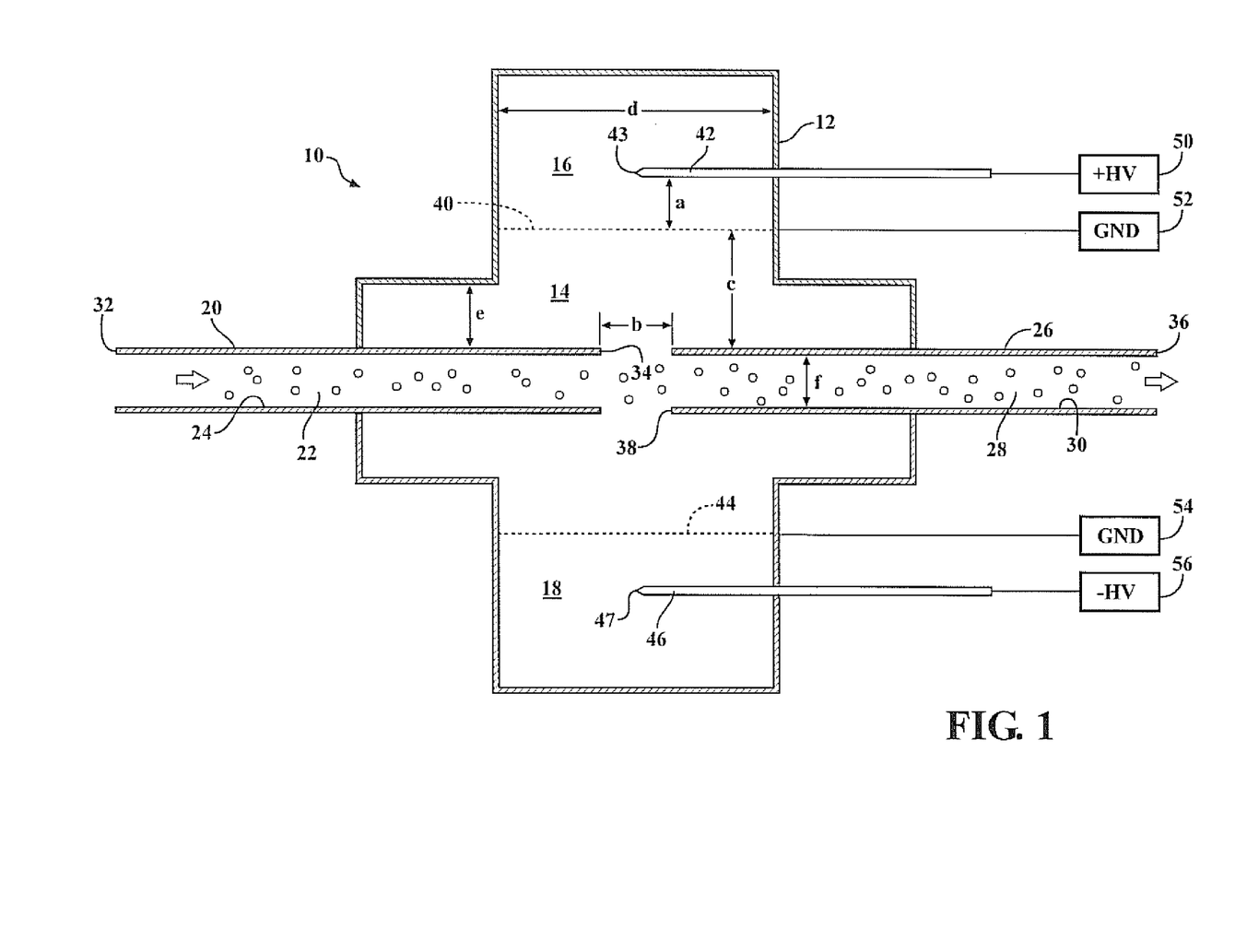
FIG. 1 is a cross-sectional view of a first embodiment of a bipolar charger in accordance with the present invention.

FIG. 1 shows a cross-sectional schematic view of a first embodiment of a bipolar charger in accordance with the present invention. The charger 10 has a housing 12 that encloses an interior space. This interior space is divided into a main chamber 14, a positive electrode chamber 16, and a negative electrode chamber 18. In the illustrated embodiment, the main chamber is the central area of the housing with the positive electrode chamber 16 and negative electrode chamber 18 being symmetrically attached to opposite sides of the main chamber 14. An inlet passage 20 allows a flow of aerosol 22 to flow into the main chamber 14. The inlet passage has an inner surface 24 formed of an electrically conductive material. In some embodiments, the inlet passage 20 is a tube formed of an electrically conductive material, such as metal. An outlet passage 26 allows a charge-conditioned aerosol 28 to flow from the main chamber 14. The outlet passage 26 has an inner surface 30 formed of an electrically conductive material. In some embodiments, the outlet passage is a metal tube. Preferably, the inlet passage 20 and the outlet passage 26 are the only openings into the housing 12, with the housing otherwise being sealed. It is desirable to avoid dilution of the aerosol or loss of particles forming the aerosol. As such, it is desirable to avoid any additional flow of gas or material into or out of the housing. As shown, the inlet passage 20 has an outer end 32 disposed outside the housing 12 and an inner end 34 in the main chamber 14. The outer end would be attached to a source of aerosol. Likewise, the outlet passage 26 has an outer end 36 disposed outside the housing 12 and an inner end 38 in the main chamber 14. The outlet end 36 would be attached to the inlet of a device requiring a charged aerosol flow.

The positive electrode chamber 16 has a ground electrode 40 and a positive electrode 42. In this embodiment, the ground electrode 40 takes the form of a ground electrode member dividing the positive electrode chamber from the main chamber 14. The negative electrode chamber 18 has a ground electrode 44 and a negative electrode 46. The ground electrode 44 takes the form of a ground electrode member dividing the negative electrode chamber 18 from the main chamber 14. In this embodiment, the positive electrode 42 and negative electrode 46 are each needle shaped with exposed tips 43 and 47, respectively. The ground electrode members 40 and 44 take the form of a mesh, a perforated plate, an orifice plate, or a screen such that the members have openings defined therethrough. Preferably, a plurality of openings are provided with each opening being small. In one example, the openings each have a size in the range of 20 micron to 1 millimeter. In some versions, the ground electrode members 40 and 44 have an opening area in the range of 20 to 90 percent of their total area. The openings in the ground electrode members 40 and 44 allow gas and ions to flow through the electrode members from the electrode chambers into the main chamber.

A power supply is connected to the high voltage electrodes 42 and 46 and the ground electrode members 40 and 44. This power supply may take a variety of forms. In FIG. 1, the power supply is represented by boxes 50, 52, 54 and 56. In some embodiments, boxes 50 and 52 represent one power supply while boxes 54 and 56 represent a second power supply, with the two power supplies representing the overall power supply for the bipolar charger. As known to those of skill in the art, the power supplies may be of various types. In one example, the power supplies include Proportional, Integral, Derivative (PID) controls for controlling corona currents. During operation of the bipolar charger 10, a positive corona current is maintained between the positive electrode 42 and the ground electrode element 40 and a negative corona current is maintained between the negative electrode 46 and the second ground electrode 44. The magnitude of corona current in each module can be in the range of a few nanoamperes to a few microamperes. Maintaining similar corona currents in both modules may be desirable, but not necessary to obtain a steady-state charge distribution. For instance, +2 μA and −2 μA can give similar results as +2 μA and −8 μA (or −2 μA and +8 μA) in some examples.

The corona currents maintained between the high voltage electrodes and their respective ground electrodes cause a creation of clouds of ions in the positive electrode chamber 16 and negative electrode chamber 18. These clouds of ions flow through the openings in the ground electrode members 40 and 44 into the main chamber 14 where they mix with the aerosol 22 to create a charged aerosol 28 with a steady-state electric charge distribution. This flow of ions is accomplished without any external flow or pumping of the ions to the main chamber. It is also noted that in these embodiments the ions from the positive and negative electrode chambers are not mixed with each other in advance of mixing the ions with the aerosol flow. Instead, ions from both chambers flow into the main chamber where they mix with the aerosol flow and may mix with each other, generally at the same time.

In the illustrated embodiment, the size and configuration of the positive electrode chamber 16 and its electrodes, and the negative electrode chamber 18 and its electrodes, are symmetrical about an axis generally defined by the inlet passage 20. The two ground electrode elements 40 and 44 are generally planar and parallel to one another, and equally spaced from the outer surfaces of the tubes 20 and 26 by a distance c. In some versions, the distance c in the range of 1 millimeter to 5 millimeter. In some embodiments, it is preferred that the aerosol 22 remain generally along a flow path defined along the inlet passage 20 and out through the outlet passage 26. The aerosol remains primarily along this path with little migration into the overall main chamber 14. As shown, the inner ends 34 and 38 of the inlet passage 20 and outlet passage 26 are spaced apart by a gap with a length labeled b. In some versions, the gap b is in the range of 2 mm to 10 mm, though other gaps may be used depending on the size of the device and other factors. In some embodiments, the inlet passage 20 and outlet passage 26 are formed as a single tube with a mid portion having openings taking the place of the gap indicated by dimension b. These openings may be generally circular with a diameter b. In each case, the gap or the openings may be small such that the majority of the particles forming the aerosol flow along the inlet passage 20, flow directly across the gap or past the openings between the inlet passage and outlet passage and out through the outlet passage 26. The mixing with the ions occurs primarily at the gap or openings. This gap or the mid portion of a tube defining the inlet and outlet passages is considered part of the main chamber 14.

In the illustrated embodiment, the inlet passage 20 and outlet passage 26 each have an inner diameter indicated by dimension f and outer surfaces spaced from the walls of the main chamber by a distance e. In some versions, the distance e is in the range from 0 to equal to the distance c.

In the illustrated embodiment, the electrode chambers 16 and 18 have a width labeled d. In one exemplary version this dimension d is about 6 mm, but other dimensions may be preferred for other versions. The high voltage electrodes run generally parallel to the flow path and are parallel to the ground electrode members 40 and 44. A distance between the high voltage electrodes and the ground electrode members is labeled a. This distance is chosen so as to provide a stable non-thermal corona discharge. In one example, the distance a is in the range of 1 mm to 2 mm. In some embodiments, the high voltage electrodes are needle shaped with a diameter in the range of 50 to 500 microns and a tip radius in the range of 5 to 100 microns. In some embodiments, the tip of each electrode is generally disposed in alignment with the center of the ground electrode. In other embodiments, the high voltage electrons may take other forms, such as not having an exposed tip but instead crossing the electrode chamber from side to side. Such a wire-shaped electrode, in some versions, may have a diameter in the range of 10 to 100 microns.

During operation, the ground electrode members 40 and 44 and the inner surfaces 24 and 30 of the passages 20 and 26 are grounded relative to the high voltage electrodes 42 and 46. The term "grounded" as used herein may mean absolute ground. However, the term "grounded", as used herein, may also mean that these elements are relatively close to absolute ground, with respect to the high voltage electrodes, but may be offset somewhat with respect to absolute ground. In one example, these elements may be in the range of ±10 to 20 volts with respect to absolute ground but are considered grounded with respect to the high voltage electrodes, which may be maintained at a positive or negative voltage in the range of 1000 to 4000 volts in some versions. Additionally, these "grounded" elements may all be at the same ground or may each be at a different ground, while still being considered "grounded" with respect to the high voltage electrodes. In one example, the power supplies maintain the ground electrodes at "ground" relative to the high voltage electrodes and the power supplies are connected to a power source such as a battery. In the same example, the inner surfaces of the inlet passage and outlet passage, or the entirety of the passages, are directly connected to the negative terminal of the power source or battery. As will be clear to those of skill in the art, the "ground" for the two ground electrodes and for the inner surfaces of the passages may each be somewhat different without substantially altering the operation of the device.

Figure 2A:
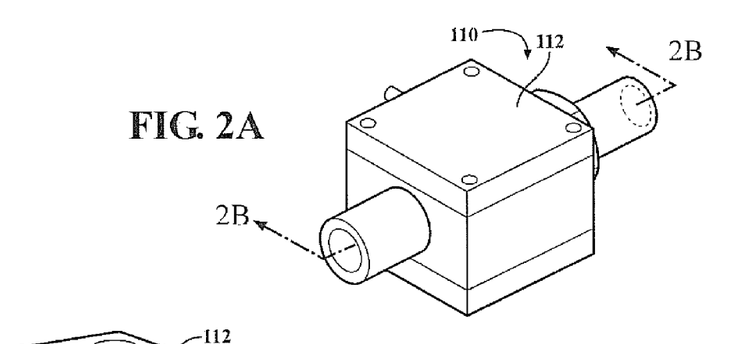
FIG. 2A is a perspective view of another embodiment of a bipolar charger in accordance with the present invention.
Figure 2B:
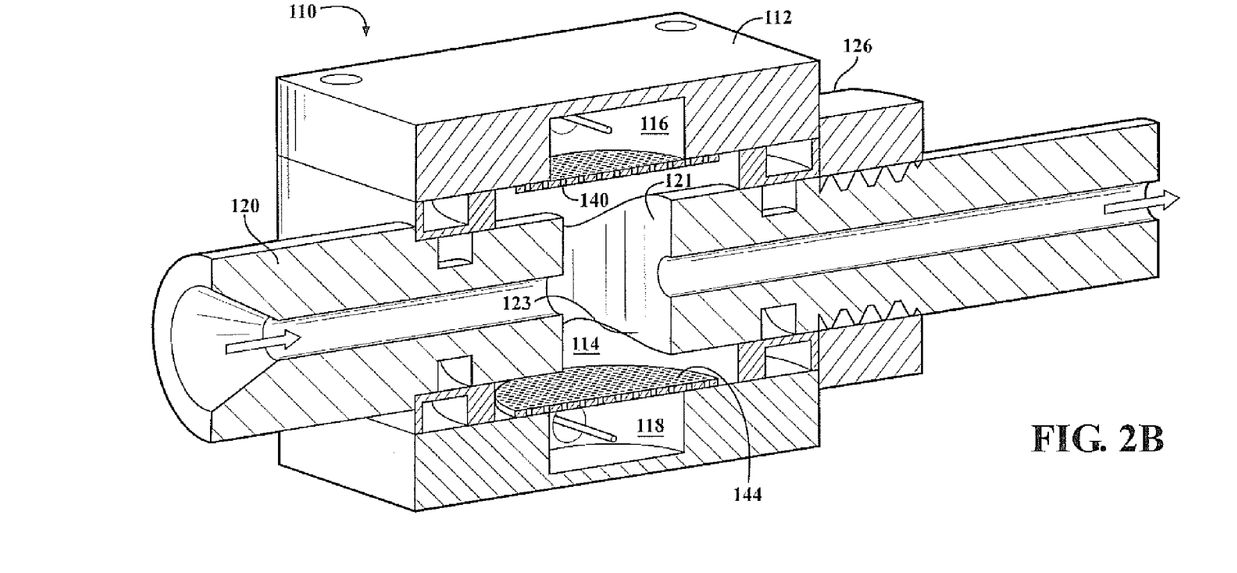
FIG. 2B is a cross-sectional perspective view of the bipolar charger of FIG. 2A, taken along lines 2B-2B.
Figure 3:
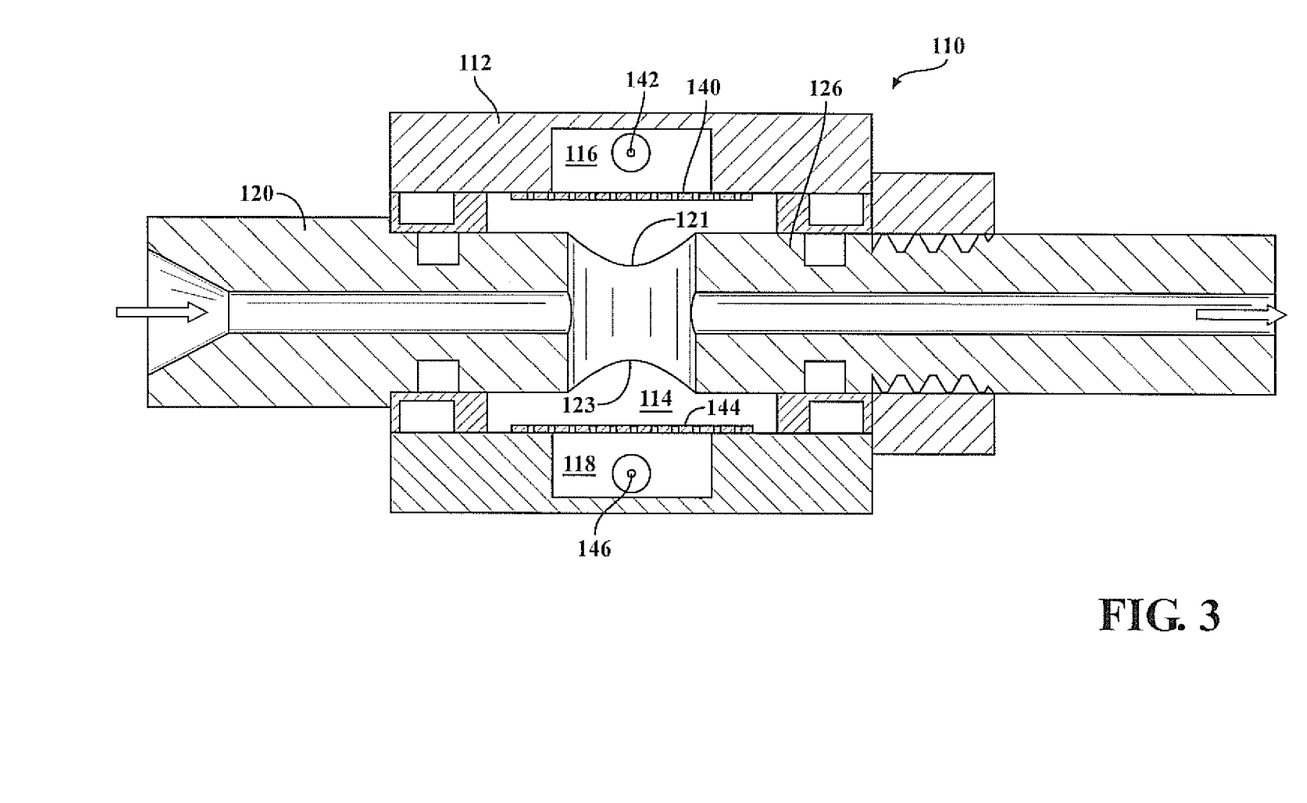
FIG. 3 is a cross-sectional view of the bipolar charger of FIGS. 2A and 2B.

Referring now to FIGS. 2A, 2B and 3, more detailed drawings of a second embodiment of a bipolar charger in accordance with the present invention will be discussed. The bipolar charger 110 has a generally cube-shaped housing 112 enclosing an interior space. Some embodiments of the present invention are suitable for miniaturization, with one example of the embodiment shown in FIG. 2A having a height of 0.65 inches and a housing length and width of 0.75 inches each. The interior space of the housing 112 is divided into a main chamber 114, a positive electrode chamber 116, and a negative electrode chamber 118. A first ground electrode element 140 divides the positive electrode chamber 116 from the main chamber 114 and a second ground electrode element 144 divides the negative electrode chamber 118 from the main chamber 114. As with the prior embodiment, the positive electrode chamber 116 and the negative electrode chamber 118 are symmetrical with respect to the main chamber 114. This embodiment differs from the prior embodiment in that the high voltage electrodes 142 and 146 extend generally perpendicular to the flow path. This embodiment also differs from the prior embodiment in that the inlet passage 120 and outlet passage 126 are formed by a single tube having a pair of openings 121 and 123 defined in a mid portion thereof. This mid portion of the tube forms part of the main chamber 114 of the bipolar charger. As shown, the openings 121 and 123 are symmetrical with respect to each other, with one of the openings facing each of the chambers 116 and 118. In this embodiment, the ground electrode elements 140 and 144 take the form of perforated plates with a plurality of openings therethrough.

Figure 4:
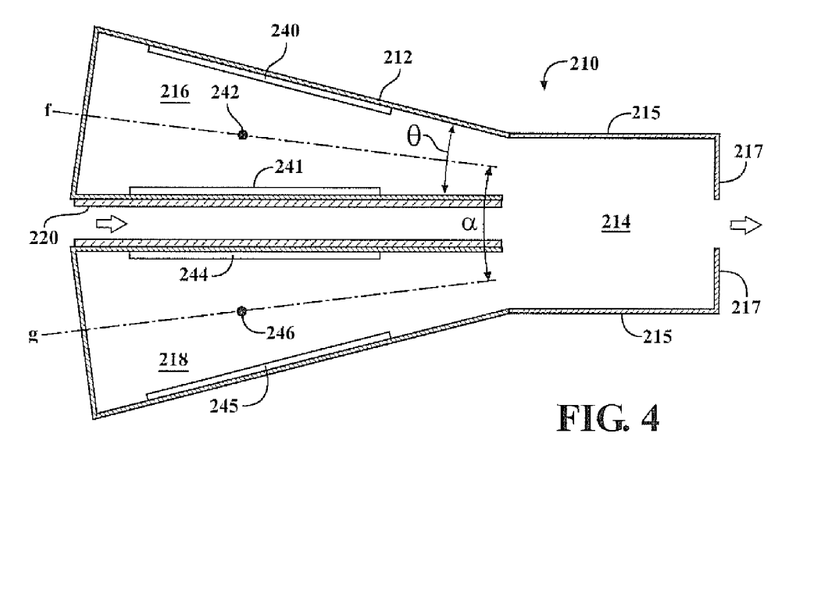
FIG. 4 is a cross-sectional view of an alternative embodiment of a bipolar charger in accordance with the present invention.

Referring now to FIG. 4, a third embodiment of a bipolar charger 210 will be discussed. The charger 210 has a housing 212 with a main chamber 214, a positive electrode chamber 216, and a negative electrode chamber 218 defined therein. An inlet passage 220 provides a flow of aerosol into the main chamber 214. In this embodiment, the outlet passage is defined by an opening in the main chamber 214. In practice, a tube may be connected thereto to provide an additional outlet passage. In this embodiment, the positive electrode chamber 216 and negative electrode chamber 218 lie alongside the inlet passage 220. In the illustrated embodiment, the high voltage electrodes 242 and 246 extend perpendicular to the axis of the inlet passage 220. Unlike in the prior embodiments, the ground electrodes for the electrode chambers do not divide the main chamber from the electrode chambers. Instead, the ground electrodes are disposed along one of the inner surfaces of each chamber. In the illustrated embodiment, the first ground electrode comprises two ground electrode plates 240 and 241 in the positive electrode chamber 216 and the second ground electrode comprises an additional two ground electrodes plates 244 and 245 in the negative electrode chamber 218. Alternatively, a single ground electrode plate, or a differently shaped ground electrode, may be used in each chamber. Alternatives include a needle-shaped or wire-shaped ground electrode. In the illustrated embodi- 
ment, the two ground electrode plates 240 and 241 or 244 and 245 form opposed surfaces of the respective electrode chambers, with each forming a portion of the inner surface of the respective electrode chamber. Preferably, the remainder of the inner surface of these electrode chambers is formed by a dielectric material. The surfaces are angled with respect to each other at an angle θ. In some embodiments, the angle θ may be in the range of 0 to 70 degrees. Preferably, the ground electrode plates are equally spaced from the respective high voltage electrode, with the high voltage electrodes being parallel to the planes that contain each of the ground electrode plates. The high voltage electrodes may also be aligned with the center of each ground electrode plate.

In the illustrated embodiment, the positive electrode chamber 216 may be said to have a chamber axis f defined midway between the ground plates and the negative electrode chamber 218 has a chamber axis g defined midway between the electrode plates. These axes are angled with respect to each other by an angle α, which in some embodiments may be in the range of 0 to 70 degrees.

In the illustrated embodiment, the walls 215 and 217 of the main chamber 214 are preferably formed, or have an inner surface fanned, of an electrically conducting material. As such, at least the walls 217 may serve as part of the outlet passage.

Figure 5:
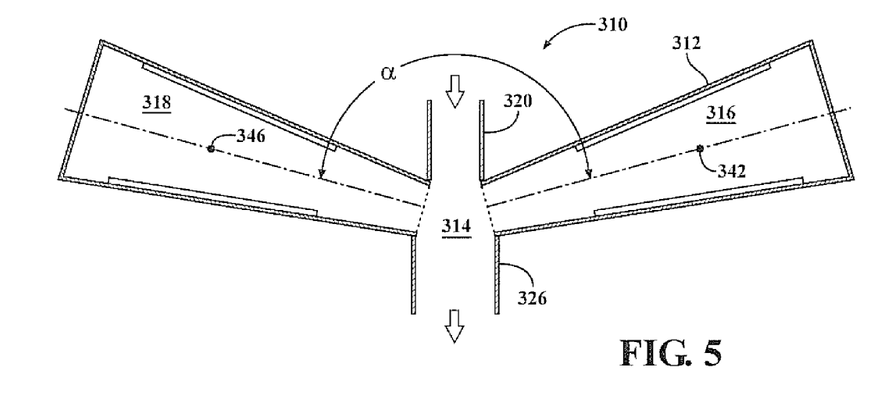
FIG. 5 is a cross-sectional view of a further alternative embodiment of a bipolar charger in accordance with the present invention.
Figure 6:
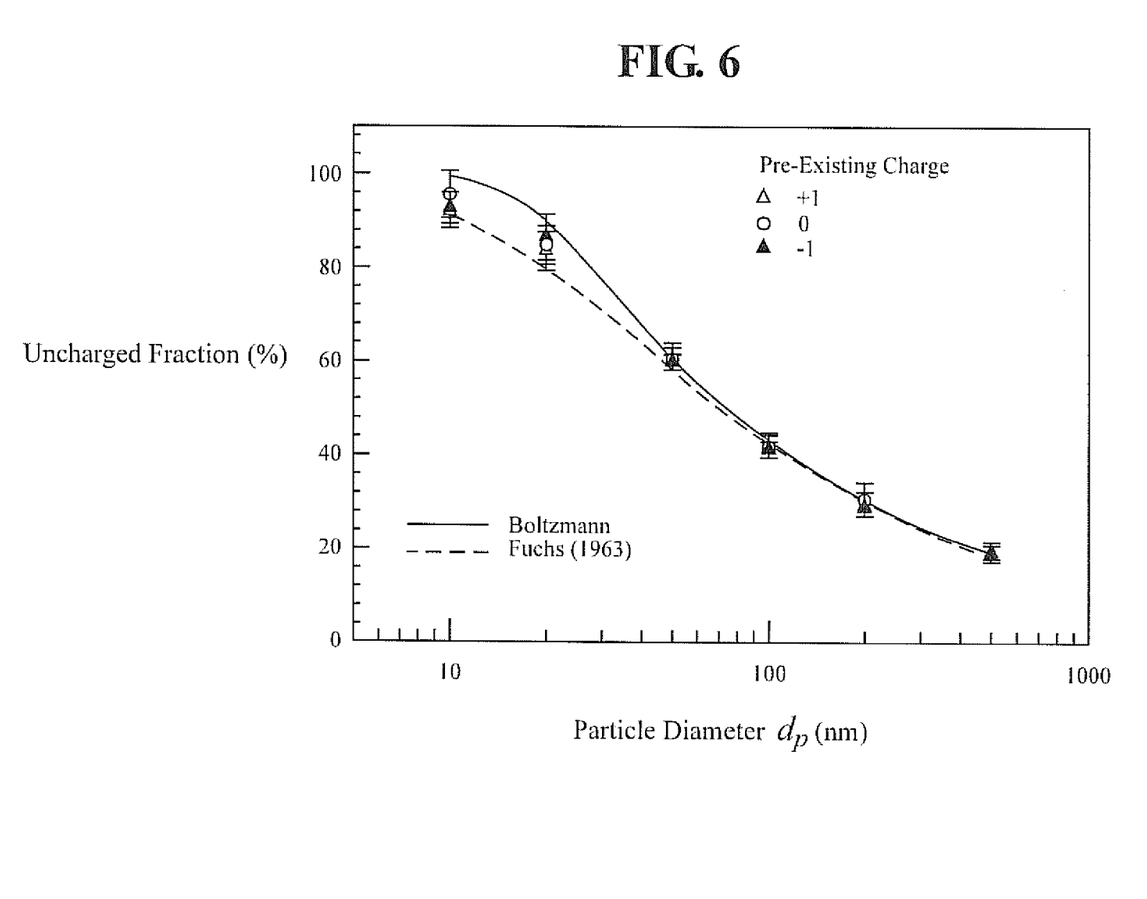
FIG. 6 is a graph showing exemplary data for uncharged fraction versus particle diameter.
Figure 7:
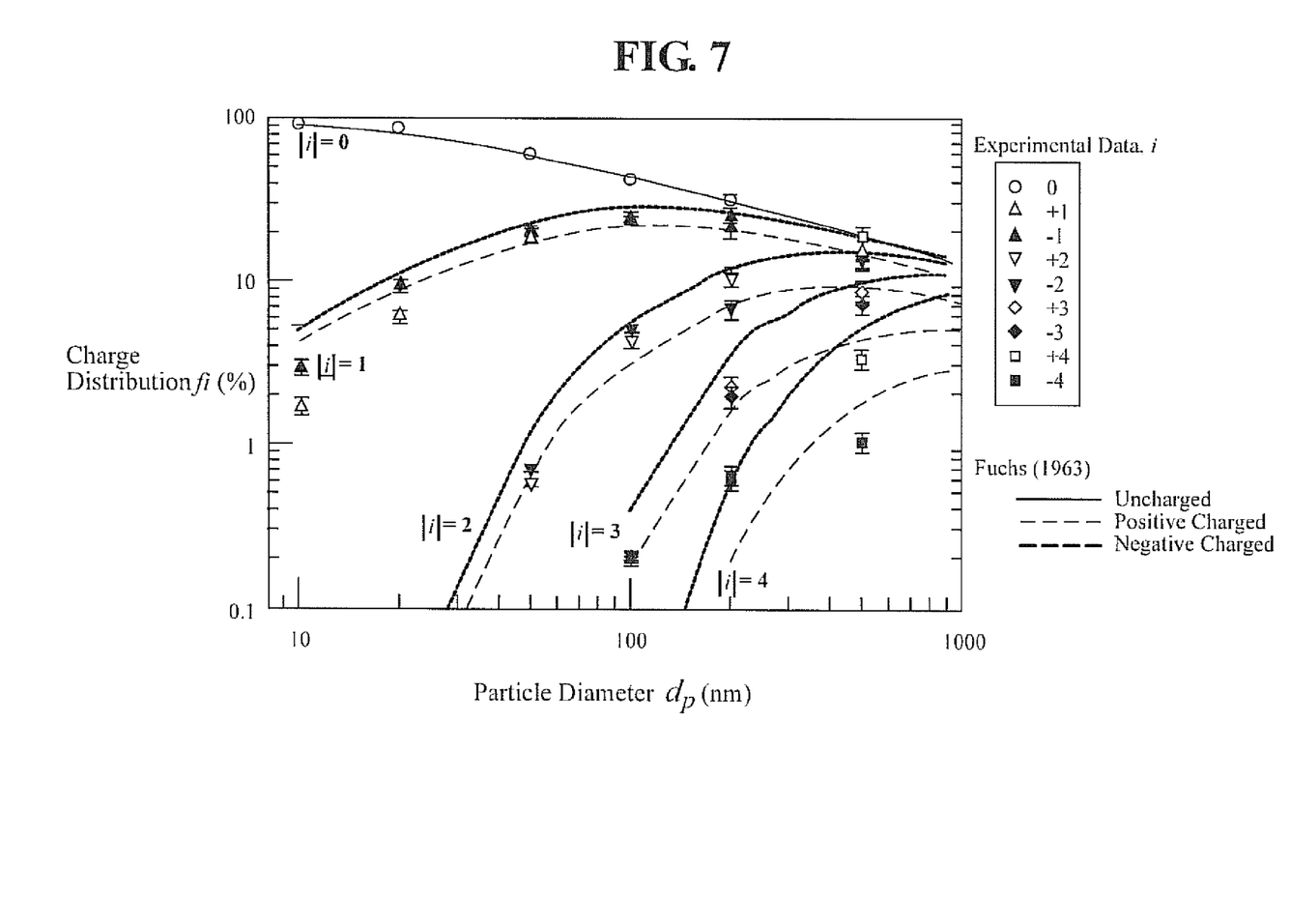
FIG. 7 is a chart showing exemplary data for percent charge distribution versus the particle diameter for particles that were originally positively charged.
Figure 8:
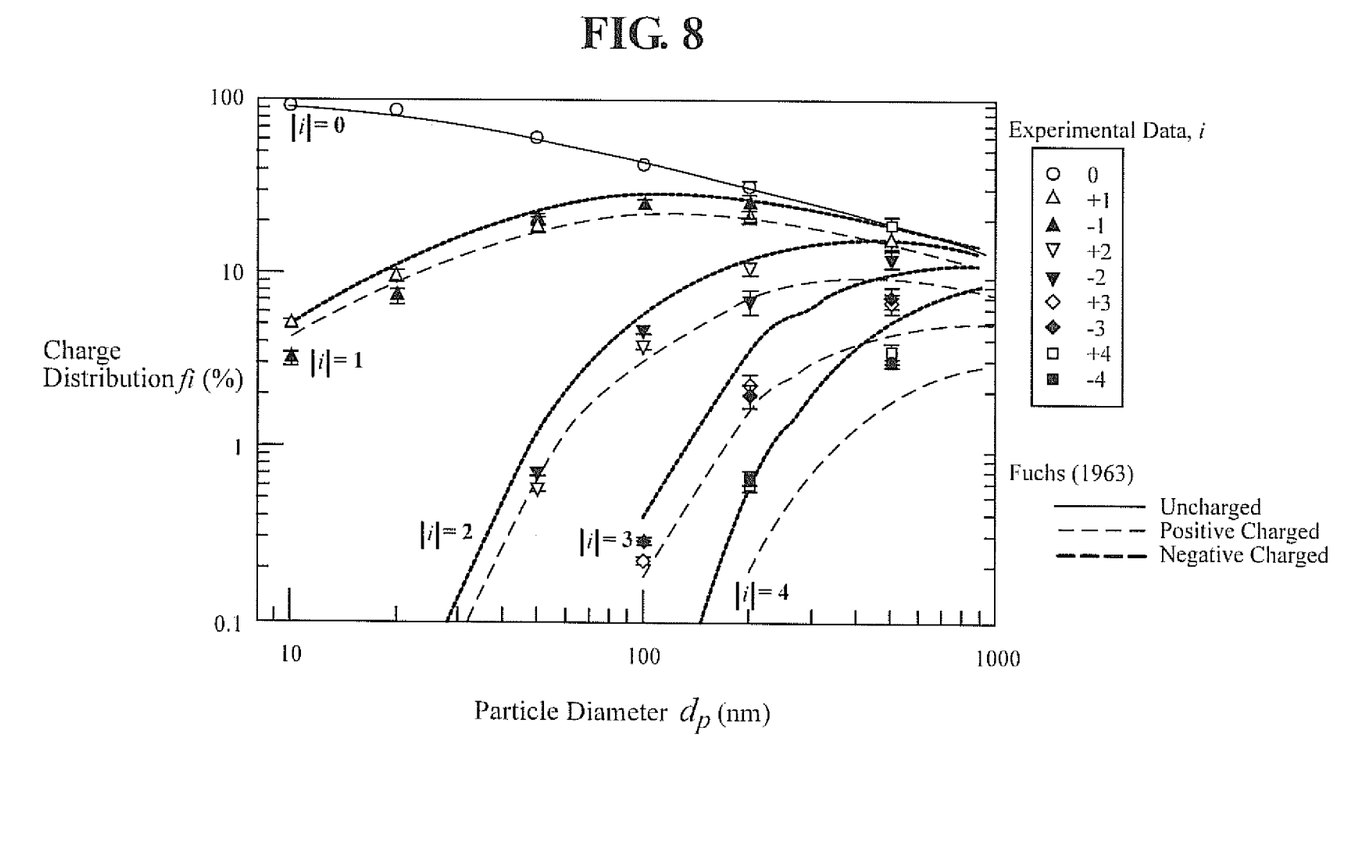
FIG. 8 is a chart showing exemplary data for percent charge distribution versus the particle diameter for particles that were originally uncharged.
Figure 9:
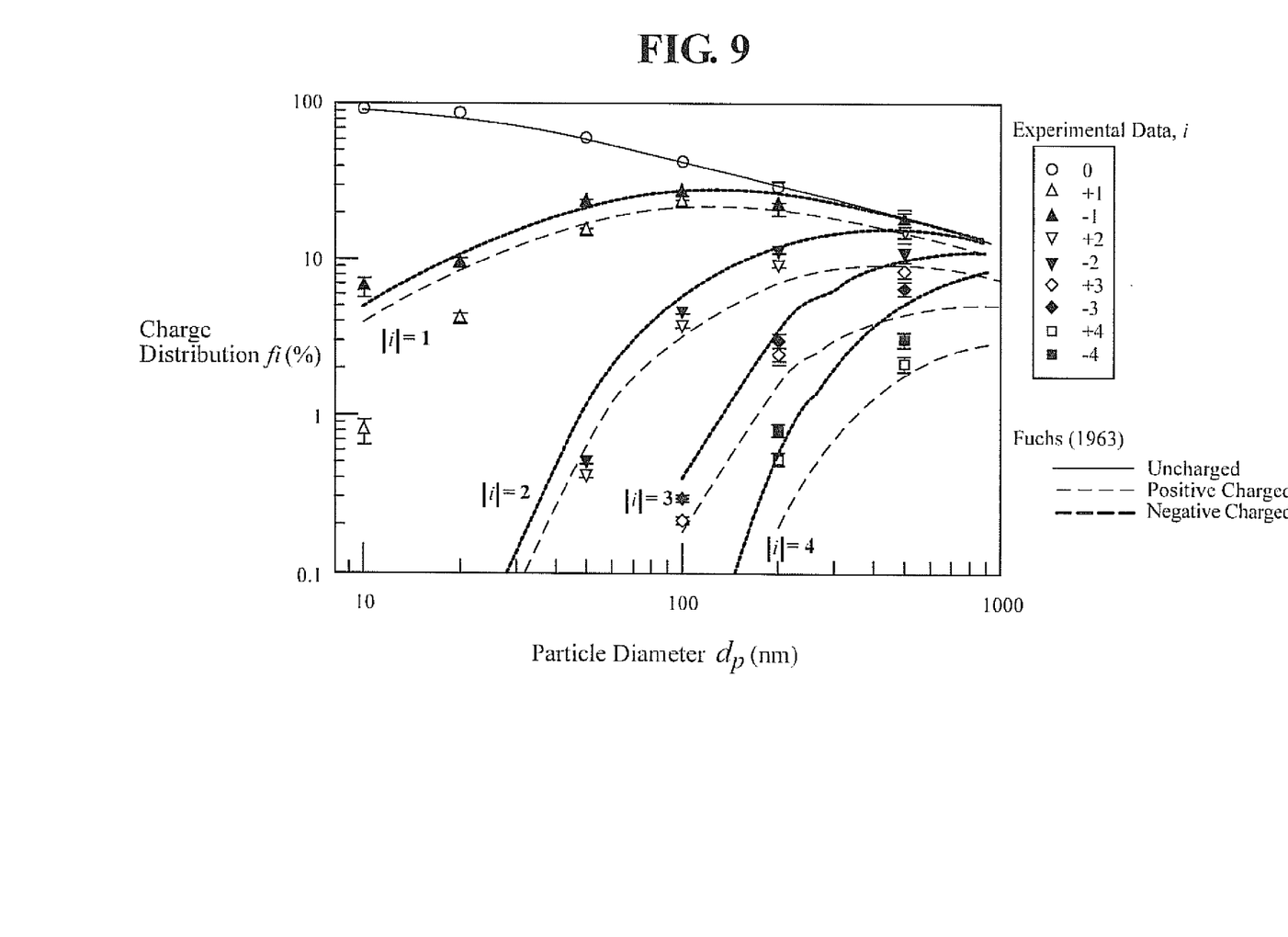
FIG. 9 is a chart showing exemplary data for percent charge distribution versus the particle diameter for particles that were originally negatively charged.

Referring now to FIG. 5, a fourth embodiment of a bipolar charger in accordance with the present invention is shown generally at 310. It has a housing 312 with a main chamber 314, a positive electrode chamber 316, and a negative electrode chamber 318 defined therein. An inlet passage is shown at 320 and an outlet passage is shown at 326. This embodiment is similar to the embodiment of FIG. 4 except that the electrode chambers are angled with respect to each other at an angle α that is much greater than in FIG. 4. However, it is preferred that the chambers be positioned such that the high voltage electrodes 342 and 346 are not directly exposed to one another. That is, a line drawn between the electrodes intersects walls of the chambers. This is desirable to eliminate any mutual interaction of high potential electrodes and possible electric field in the aerosol flow path.

In preferred embodiments of the present invention, the high voltage electrodes are positioned out of flow path. This helps to prevent contamination of the high voltage electrodes. Also, preferred embodiments of the present invention are configured such that the electrical fields created by the electrode chambers are spaced from the flow path such that the electrical fields do not substantially influence the particles of an aerosol. As known to those of skill in the art, particles of an aerosol may carry a positive or negative charge prior to mixing with the ions in the main chamber, and may carry a different charge after mixing with the ions. In the presence of an electrical field, these charged particles may be influenced such as by altering their path. In preferred embodiments of the present invention, this is reduced or avoided by positioning the high voltage electrodes and the electrical fields associated with them in electrode chambers to the sides of the main chamber. This improves the transmission efficiency of the charger.

The FIG. 6 shows uncharged fraction ($f_0$) as a function of particle size obtained experimentally from an exemplary version of a bipolar charger in accordance with the present invention. Also, shown for comparison are calculated curves from Boltzmann statistics and Fuchs theory corresponding to a steady-state charge equilibrium. The aerosol flow rate in the bipolar charger was 0.3 L/min and the two corona ionizers were operated at +5 μA and −5 μA corona currents, respectively. The error bar on each data point represents the standard deviation over three replicate measurements. The figure demonstrates that the test particles, carrying different pre-existing charges of +1, 0 and −1, all acquire the same steady-state uncharged fraction after passing through the bipolar charger (irrespective of the level of pre-existing charge).

The overall charge distribution for all the test particles studied in this example are presented in FIGS. 7-9. FIG. 7 is for particles that were originally positively charged, FIG. 8 is for particles that were originally uncharged, and FIG. 9 is for particles that were originally negatively charged. The charge distribution function provides, for a given particles size, a number-weighted distribution of charge levels in the particle population (i.e. x % of particles carrying 0 charge, y % carrying +1 z % carrying +2, and so on . . . ). The charge distribution calculated from Fuchs theory is also shown to illustrate the difference between distributions in positively and negatively charged fractions. As shown in the figure, in general, the experimental charge distributions from the exemplary charger, regardless of the pre-existing charge level, agrees very well with the theoretical distributions from Fuchs theory. This figure provides strong experimental evidence that the charge distributions from the charger are steady-state, quasi-Boltzmann distributions and the charger functions as a bipolar charger.

Numerous alternatives to the illustrated embodiments are possible. For example, while the illustrated embodiments have symmetrical positive and negative electrode chambers, the chambers may be non-symmetrical. Further, the dimensions provided herein may be altered depending on the size and characteristics of the charger. As will be clear to those of skill in the art, the system may be tuned, by adjusting the corona currents and other factors, in order to obtain the desired performance characteristics.

As will be clear to those of skill in the art, the herein described and illustrated embodiments of the present invention may be altered in various ways without departing from the scope or teaching of the present invention. It is the following claims, including all equivalents, which define the scope of the present invention.

The invention claimed is:

1. A bipolar charger for charging particles of a flow of aerosol, the bipolar charger comprising:

a housing having a main chamber, a positive electrode chamber and a negative electrode chamber defined therein, the electrode chambers each being directly connected to the main chamber, the electrode chambers each having an inner surface;

an inlet passage for providing a flow of aerosol into the main chamber, the inlet passage having an inner surface formed of an electrically conductive material;

an outlet passage for charged aerosol to flow from the main chamber, the outlet passage having an inner surface formed of an electrically conductive material;

a flow path for the aerosol being defined from the inlet passage, through the main chamber, and out of the outlet passage;

a first ground electrode disposed in the positive electrode chamber;

a positive electrode disposed in the positive electrode chamber and spaced from the first ground electrode;

a second ground electrode disposed in the negative electrode chamber;

a negative electrode disposed in the negative electrode chamber and spaced from the second ground electrode;

a power supply interconnected with the first and second ground electrodes and the positive and negative electrodes;

a first corona current being maintained between the positive electrode and the first ground electrode such that the positive electrode is at a high positive potential with respect to the first ground electrode and the positive electrode and the first ground electrode cooperate to create a cloud of positive ions;

a second corona current being maintained between the negative electrode and the second ground electrode such that the negative electrode is at a high negative potential with respect to the second ground electrode and the negative electrode and the second ground electrode cooperate to create a cloud of negative ions;

the first and second ground electrodes and the inner surfaces of the inlet and outlet passages being grounded relative to the positive and negative electrodes; and the positive electrode chamber and the negative electrode chamber each being in gaseous communication with the main chamber such that particles of an aerosol passing along the flow path through the main chamber interact with the ions, thereby creating a flow of aerosol with a steady-state electric charge distribution.

2. A bipolar charger in accordance with claim 1, wherein the first ground electrode defines a portion of the inner surface of the positive electrode chamber and the second ground electrode defines a portion of the inner surface of the negative electrode chamber.

3. A bipolar charger in accordance with claim 2, wherein the inner surfaces of the electrode chambers not defined by the ground electrodes are formed of a dielectric material.

4. A bipolar charger in accordance with claim 2, wherein:
the first ground electrode comprises a pair of electrode plates each defining portions of the inner surface of the positive electrode chamber, each of the electrode plates being spaced from the positive electrode; and
the second ground electrode comprises a pair of electrode plates each defining portions of the inner surface of the negative electrode chamber, each of the electrode plates being spaced from the negative electrode.

5. A bipolar charger in accordance with claim 4, wherein:
the electrode plates in the positive electrode chamber define opposed inner surfaces, the surfaces being angled with respect to each other at an angle in the range of 0 to 70 degrees; and
the electrode plates in the negative electrode chamber define opposed inner surfaces, the surfaces being angled with respect to each other at an angle in the range of 0 to 70 degrees.

6. A bipolar charger in accordance with claim 5, wherein:
the positive and negative electrodes each have a longitudinal axis that is parallel to planes containing the electrode plates.

7. A bipolar charger in accordance with claim 5, wherein:
each electrode chamber has a chamber axis defined midway between the ground plates, the chamber axis of the positive electrode chamber being angled with respect to the chamber axis of the negative electrode chamber at an angle in the range of 0 to 70 degrees.

8. A bipolar charger in accordance with claim 1, wherein:
the inlet passage has an inlet axis; and
the electrode chambers are symmetrical with respect to the inlet axis and are configured such that the positive electrode is not directly exposed to the negative electrode.

9. A bipolar charger in accordance with claim 1, wherein:
the first ground electrode is a member dividing the positive electrode chamber from the main chamber; and
the second ground electrode is a member dividing the negative electrode chamber from the main chamber;

the members each having a plurality of openings defined therethrough such that the clouds of ions may pass through the openings from the electrode chambers to the main chamber.

10. A bipolar charger in accordance with claim 9, wherein:
the openings in the electrode members each have an opening size in the range of 0.1 micron to 200 microns; and
each of the electrode members have an open area in the range of 20 to 90% of their total area.

11. A bipolar charger in accordance with claim 1, wherein:
the inlet passage and outlet passage comprise a tube with a mid portion defined between an inlet portion and an outlet portion, the inlet portion defining the inlet passage and the outlet portion defining the outlet passage, the mid portion forming part of the main chamber of the housing, the mid portion having at least one opening defined therein such that particles of the flow of aerosol along the flow path interact with ions in the main chamber.

12. A bipolar charger in accordance with claim 11, wherein:
the tube is a metal tube and the at least one opening comprises a pair of opposed openings, each opening facing one of the electrode chambers.

13. A bipolar charger in accordance with claim 1, wherein:
the positive and negative electrodes are each needle shaped with an exposed tip, the electrodes having a diameter in the range of 50 to 500 microns and a tip radius in the range of 5 to 100 microns.

14. A bipolar charger in accordance with claim 1, wherein:
the power supply comprises two power supplies, each power supply providing the corona current to one of the positive or negative electrodes, the corona currents being in the range of 1 to 10 microamperes;
the power supplies each further comprising a Proportional, Integral, Derivative (PID) control for controlling the corona current.

15. A bipolar charger for charging particles of a flow of aerosol, the bipolar charger comprising:
a housing having a main chamber, a positive electrode chamber and a negative electrode chamber defined therein, the electrode chambers each having an inner surface;
a first ground electrode member disposed in the housing so as to divide the positive electrode chamber from the main chamber, the first ground electrode member defining a portion of the inner surface of the positive electrode chamber;
a second ground electrode member disposed in the housing so as to divide the second electrode chamber from the main chamber, the second ground electrode member defining a portion of the inner surface of the negative electrode chamber;
an inlet passage for providing a flow of aerosol into the main chamber, the inlet passage having an inner surface formed of an electrically conductive material;
an outlet passage for charged aerosol to flow from the main chamber, the outlet passage having an inner surface formed of an electrically conductive material;
a flow path for the aerosol being defined from the inlet passage, through the main chamber, and out of the outlet passage;
a positive electrode disposed in the positive electrode chamber and spaced from the first ground electrode member;

a negative electrode disposed in the negative electrode chamber and spaced from the second ground electrode member;

a power supply interconnected with the first and second ground electrodes and the first and second high voltage electrodes;

a first corona current being maintained between the positive electrode and the first ground electrode member such that the positive electrode is at a high positive potential with respect to the first ground electrode member and the positive electrode and the first ground electrode member cooperate to create a cloud of positive ions;

a second corona current being maintained between the negative electrode and the second ground electrode member such that the negative electrode is at a high negative potential with respect to the second ground electrode member and the negative electrode and the second ground electrode member cooperate to create a cloud of negative ions;

the ground electrode members each having a plurality of openings defined therethrough such that the clouds of ions may pass through the openings from the electrode chambers to the main chamber;

the first and second ground electrode members and the inner surfaces of the inlet and outlet passages being grounded relative to the positive and negative electrodes; and the positive electrode chamber and the negative electrode chamber each being in gaseous communication with the main chamber through the openings in the ground electrode members such that particles of an aerosol passing through the main chamber interact with the ions, thereby creating a flow of aerosol with a steady-state electric charge distribution.

16. A bipolar charger in accordance with claim 15, wherein:

the inlet passage and outlet passage comprise a tube with a mid portion defined between an inlet portion and an outlet portion, the inlet portion defining the inlet passage and the outlet portion defining the outlet passage, the mid portion forming part of the main chamber of the housing, the mid portion having at least one opening defined therein such that particles of the flow of aerosol along the flow path interact with ions in the main chamber.

17. A bipolar charger in accordance with claim 16, wherein:

the tube is generally parallel to the ground electrode members, the ground electrode members being spaced from an outer surface of the tube by a distance in the range of 1 mm to 5 mm.

18. A bipolar charger in accordance with claim 15, wherein:

the electrode members comprise a mesh, a perforated plate, an orifice plate or a screen;

the openings in the electrode members each have an opening size in the range of 0.1 micron to 200 microns; and each of the electrode members have an open area in the range of 20 to 90% of their total area.

19. A method of providing a state-state charge distribution to a flow of aerosol, comprising:

providing a bipolar charger for charging particles of a flow of aerosol, the bipolar charger comprising:

a housing having a main chamber, a positive electrode chamber and a negative electrode chamber defined therein, the positive electrode chamber and the negative electrode chamber each being directly connected to and in gaseous communication with the main chamber, the electrode chambers each having an inner surface;

an inlet passage for providing a flow of aerosol into the main chamber, the inlet passage having an inner surface formed of an electrically conductive material;

an outlet passage for charged aerosol to flow from the main chamber, the outlet passage having an inner surface formed of an electrically conductive material;

a flow path for the aerosol being defined from the inlet passage, through the main chamber, and out of the outlet passage;

a first ground electrode disposed in the positive electrode chamber;

a positive electrode disposed in the positive electrode chamber and spaced from the first ground electrode;

a second ground electrode disposed in the negative electrode chamber;

a negative electrode disposed in the negative electrode chamber and spaced from the second ground electrode;

providing a flow of aerosol along the flow path;

maintaining a first corona current between the positive electrode and the first ground electrode such that the positive electrode is at a high positive potential with respect to the first ground electrode and the positive electrode and the first ground electrode cooperate to create a cloud of positive ions;

maintaining a second corona current between the negative electrode and the second ground electrode such that the negative electrode is at a high negative potential with respect to the second ground electrode and the negative electrode and the second ground electrode cooperate to create a cloud of negative ions; and grounding the first and second ground electrodes and the inner surfaces of the inlet and outlet passages relative to the positive and negative electrodes;

whereby particles of the aerosol passing along the flow path through the main chamber interact with the ions from the electrode chambers, thereby creating a flow of aerosol with a steady-state electric charge distribution.

\* \* \* \* \*